United States Patent [19]
Chatterjee

[11] Patent Number: 5,827,877
[45] Date of Patent: Oct. 27, 1998

[54] KETOMETHYLENE GROUP-CONTAINING CYSTEINE AND SERINE PROTEASE INHIBITORS

[75] Inventor: Sankar Chatterjee, Wynnewood, Pa.

[73] Assignee: Cephalon, Inc., West Chester, Pa.

[21] Appl. No.: 646,071

[22] Filed: May 7, 1996

Related U.S. Application Data

[60] Provisional application No. 60/003,678 Sep. 14, 1995.
[51] Int. Cl.⁶ .......................... A01N 43/16; C07D 311/82
[52] U.S. Cl. ............................................ 514/454; 549/388
[58] Field of Search .............................. 549/388; 514/454

[56] References Cited

U.S. PATENT DOCUMENTS

| | | | |
|---|---|---|---|
| 4,518,528 | 5/1985 | Rasnick | 260/112.5 R |
| 5,081,284 | 1/1992 | Higuchi et al. | 560/159 |
| 5,328,916 | 7/1994 | Raddatz et al. | 514/318 |
| 5,444,042 | 8/1995 | Bartus et al. | 514/2 |
| 5,498,616 | 3/1996 | Mallamo et al. | 514/300 |
| 5,498,728 | 3/1996 | Sohda et al. | 548/493 |
| 5,545,640 | 8/1996 | Beaulieu et al. | 514/311 |

FOREIGN PATENT DOCUMENTS

| | | |
|---|---|---|
| 363284A2 | 4/1990 | European Pat. Off. . |
| 520336A2 | 12/1992 | European Pat. Off. . |
| WO 92/11850 | 7/1992 | WIPO . |
| WO 92/12140 | 7/1992 | WIPO . |
| WO 94/00095 | 1/1994 | WIPO . |
| WO 94/08941 | 4/1994 | WIPO . |
| WO 94/21673 | 9/1994 | WIPO . |
| WO 95/00535 | 1/1995 | WIPO . |
| WO 95/24914 | 9/1995 | WIPO . |

OTHER PUBLICATIONS

Chatterjee et al., Xanthene Derived Potent Nonpeptidic Inhibitors of Recombinant Human Calpain I., Biorganic & Medicinal Chem. Letters, vol. 6, No. 13, 1996, pp. 1619–1622.

Sebastian et al., Effect of Enzyme–Substrate Interactions Away From the Reaction Site On Carboxy Peptidase A Catalysis, Biorganic Chem., vol. 24, No. 3, 1996, pp. 290–303.

Angliker, H. et al., "Inactivation of Calpain by Peptidyl Fluoromethyl Ketones", *J. Med. Chem.* 1992, 35, 216–220.

Greene and Wuts, "Protective Groups in Organic Synthesis", 2nd Edition, Wiley & sons, 1991.

Hamada, Y. et al., "Efficient Total Synthesis of Didemnins A and †,1", *J. Am. Chem. Soc.* 1989, 111, 669–673.

Harbeson, S. et al., "Stereospecific Synthesis of Peptidyl α–Keto Amides as Inhibitors of Calpain", *J. Med. Chem.* 1994, 37, 2918–2929.

Harris, B. et al., "Synthetic Studies of Didemnins. II. Approaches to Statine Diastereomers", *Tetrahedron Letters* 1987, 28(25), 2837–2840.

Hoffman, R. V. et al., "A New Chiral Alkylation Methodology for the Synthesis of 2–Alky–4Ketoacids in High Optical Purity Using 2–Triflyloxy Esters", *Tetrahedron Letters* 1993, 34(13), 2051.

Hoffman, R.V. and Kim, "The Stereoselective Synthesis of 2–Alkyl γ–Keto Acid and Heterocyclic Ketomethylene Peptide Isostere Core Units using Chiral Alkylation by 2–Triflyloxy Esters", *J. Org. Chem.* 1995, 60, 5107–5113.

Imperiali, B. and Abeles, "A Versatile Synthesis of Peptidyl Fluoromethyl Ketones", *Tetrahedron Letters* 1986, 27(2), 135–138.

Lee, W.J. et al., "Factors Influencing the Binding of Calpain I to Human Erythrocyte Inside–Out Vesicles", *Biochemistry International* 1990, 22(1), 163–171.

Lehninger, "Biochemistry", 2nd Edition, Worth Publishers, 1975, pp. 73–75.

Luly, J.R. et al., "A Synthesis of Protected Aminoalkyl Epoxides from γ–Amino Acids", *J. Org. Chem.* 1987, 52, 1487–1492.

Patel, D. et al., "Activated Ketone Based Inhibitors of Human Renin", *J. of Medicinal Chem.* Aug. 20, 1993, 36(17), 2431–2447.

"Remington's Pharmaceutical Sciences", Mack Publishing Co., Easton, PA, 1980.

Revesz, L. et al., "Synthesis of P1 Aspartate–Based Peptide Acyloxymethyl and Fluoromethyl Ketones as Inhibitors of Interleukin–1β–Converting Enzyme", *Tetrahedron Letters* 1994, 35(52), 9693–9696.

Tung, R. and Rich, "Bis(2–oxo–3–oxazolidinyl) phosphinic Chloride (1) as a Coupling Reagent for N–Alkyl Amino Acids", *J. Am. Chem. Soc.* 1985, 107, 4342–4343.

*Primary Examiner*—Mukund J. Shah
*Assistant Examiner*—Tamthom T. Ngo
*Attorney, Agent, or Firm*—Woodcock Washburn Kurtz MacKiewicz & Norris LLP

[57] ABSTRACT

The present invention is directed to novel ketomethylene group-containing inhibitors of cysteine or serine proteases. Methods for the use of the protease inhibitors are also described.

8 Claims, No Drawings

KETOMETHYLENE GROUP-CONTAINING CYSTEINE AND SERINE PROTEASE INHIBITORS

CROSS REFERENCE TO RELATED APPLICATIONS

This application claims benefit of U.S. Provisional Application Ser. No. 60/003,678, filed Sep. 14, 1995.

FIELD OF THE INVENTION

Novel ketomethylene group-containing inhibitors of cysteine or serine proteases, methods for making these novel compounds, and methods for using the same are disclosed.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy.

The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypanosoma cruzi*, malaria parasites *Plasmodium falciparum* and *P.vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine.

The present invention is directed to these, as well as other, important ends.

SUMMARY OF THE INVENTION

The present invention is directed to novel cysteine and serine protease inhibitors which contain a ketomethylene group adjacent to the P2 position. They are represented by the following Formula I:

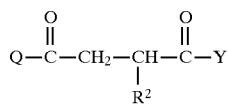

wherein:

Q is aryl having from about 6 to about 14 carbons, heteroaryl having from about 6 to about 14 ring atoms, aralkyl having from about 7 to about 15 carbons, alkyl having from 1 to about 10 carbons, said alkyl groups being optionally substituted with one or more J groups, heteroalkyl having from 2 to about 7 carbons, arylheteroalkyl wherein the aryl portion can be unfused or fused with the heteroalkyl ring, alkoxy having from 1 to about 10 carbons, aralkyloxy having from about 7 to about 15 carbons, a carbohydrate moiety optionally containing one or more alkylated hydroxyl groups, xanthene-9-yl, $CH(i\text{-}C_4H_9)NHCbz$, $CH_2N(i\text{-}C_4H_9)Cbz$, or Formula II or III:

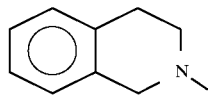

or

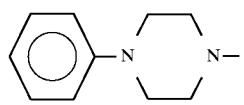

Y has the formula:

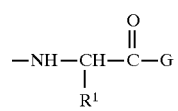

wherein:
$R^1$ and $R^2$ are independently H, alkyl having from one to about 14 carbons, cycloalkyl having from 3 to about carbons, or a natural or unnatural side chain of an L-amino acid, said alkyl and cycloalkyl groups being optionally substituted with one or more J groups;

J is halogen, lower alkyl, aryl, heteroaryl, amino optionally substituted with one to three aryl or lower alkyl groups, guanidino, alkoxycarbonyl, aralkoxycarbonyl, alkoxy, hydroxy, or carboxy; and G is hydrogen, C(=O)NR³R⁴, C(=O)OR³ or CH₂R⁵; wherein:

R³ and R⁴ are each independently hydrogen, alkyl having from 1 to about 10 carbons, said alkyl groups being optionally substituted with one or more J groups, aryl having from about 6 to about 14 carbons, and aralkyl having from about 7 to about 15 carbons; and R⁵ is halogen;

with the proviso that if G is hydrogen and Q is alkyl substituted with J, and said J is an α-amino group, then the α-amino nitrogen must be tertiary (that is, trisubstituted with other than hydrogen).

Preferred embodiments of the compounds of Formula I include those wherein R² is isobutyl, R¹ is isobutyl, benzyl, or ethyl, G is hydrogen, C(=O)NHC₂H₅, or CH₂F, and Q is as previously defined.

The compounds of the invention are useful for the inhibition of cysteine and serine proteases. Beneficially, the compounds find utility in a variety of settings. For example, in a research arena, the claimed compounds can be used, for example, as standards to screen for natural and synthetic cysteine protease and serine protease inhibitors which have the same or similar functional characteristics as the disclosed compounds. In a clinical arena, our compounds can be used to alleviate, mediate, reduce and/or prevent disorders which are associated with abnormal and/or aberrant activity of cysteine proteases and/or serine proteases. Accordingly, methods for using the subject compounds, such as methods for inhibiting serine proteases or cysteine proteases comprising contacting said proteases with an inhibitory amount of a compound of the invention are disclosed. Methodologies for making our ketomethylene group-containing inhibitors are also disclosed. These and other features of the compounds of the subject invention are set forth in more detail below.

DETAILED DESCRIPTION

Novel cysteine and serine protease inhibitors have been discovered which are represented by the general Formula I:

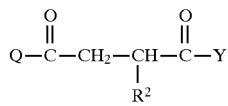

wherein:

Q is aryl having from about 6 to about 14 carbons, heteroaryl having from about 6 to about 14 ring atoms, aralkyl having from about 7 to about 15 carbons, alkyl having from 1 to about 10 carbons, said alkyl groups being optionally substituted with one or more J groups, heteroalkyl having from 2 to about 7 carbons, arylheteroalkyl wherein the aryl portion can be unfused or fused with the heteroalkyl ring, alkoxy having from 1 to about 10 carbons, aralkyloxy having from about 7 to about 15 carbons, a carbohydrate moiety optionally containing one or more alkylated hydroxyl groups, xanthene-9-yl, CH(i-C₄H₉)NHCbz, CH₂N(i-C₄H₉)Cbz, or Formula II or III:

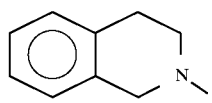

or

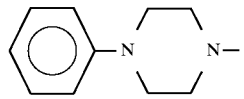

Y has the formula

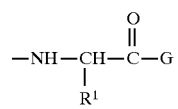

wherein:

R¹ and R² are independently H, alkyl having from one to about 14 carbons, cycloalkyl having from 3 to about 10 carbons, or a natural or unnatural side chain of an L-amino acid, said alkyl and cycloalkyl groups being optionally substituted with one or more J groups;

J is halogen, lower alkyl, aryl, heteroaryl, amino optionally substituted with one to three aryl or lower alkyl groups, guanidino, alkoxycarbonyl, aralkoxycarbonyl, alkoxy, hydroxy, or carboxy; and G is hydrogen, C(=O)NR³R⁴, C(=O)OR³ or CH₂R⁵; wherein:

R³ and R⁴ are each independently hydrogen, alkyl having from 1 to about 10 carbons, said alkyl groups being optionally substituted with one or more J groups, aryl having from about 6 to about 14 carbons, and aralkyl having from about 7 to about 15 carbons; and R⁵ is halogen;

with the proviso that if G is hydrogen and Q is alkyl substituted with J, and said J is an α-amino group, then the α-amino nitrogen must be tertiary.

In some preferred embodiments of the compounds of Formula I, R² is isobutyl. In other preferred embodiments of the compounds of Formula I, R¹ is isobutyl, benzyl, or ethyl. In further preferred embodiments of the compounds of Formula I, G is hydrogen, C(=O)NHC₂H₅, or CH₂F.

Preferably, Q is —(CH₂)₄—C₆H₅, diphenylmethyl, xanthen-9-yl or Q has the Formula II or III:

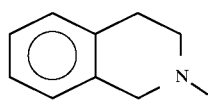

or

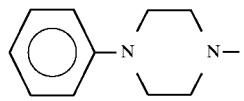

In further preferred embodiments Q is —CH(C₂H₅)(C₆H₅) or —CH(i-C₄H₉)NHCbz, with —(S)—CH(C₂H₅)(C₆H₅) and —(S)—CH(i-C₄H₉)NHCbz being particularly preferred.

In especially preferred embodiments R² is isobutyl, R¹ is isobutyl or benzyl, G is hydrogen, —CH₂F or —C(=O)NHC₂H₅, and Q is —(CH₂)₄—C₆H₅, diphenylmethyl, xanthen-9-yl, —(S)—CH(C₂H₅)(C₆H₅), or Q has the Formula II or III above.

As used herein, the term "alkyl" is meant to include straight-chain, branched and cyclic hydrocarbon groups such as, for example, ethyl, isopropyl and cyclopropyl groups. Preferred alkyl groups have 1 to about 10 carbon atoms. "Cycloalkyl" groups are cyclic alkyl groups. "Aryl" groups are aromatic cyclic compounds including but not limited to phenyl, tolyl, naphthyl, anthracyl, phenanthryl, pyrenyl, and xylyl. Preferred aryl groups include phenyl and naphthyl. The term "carbocyclic", as used herein, refers to cyclic groups in which the ring portion is composed solely of carbon atoms. The term "heterocyclic" refers to cyclic groups in which the ring portion includes at least one heteroatom such as O, N or S. "Heteroalkyl" groups are heterocycles containing solely single bonds within their ring portions, i.e. saturated heteroatomic ring systems. The term "lower alkyl" refers to alkyl groups of 1–4 carbon atoms. The term "halogen" refers to F, Cl, Br, and I atoms.

The term "aralkyl" denotes alkyl groups which bear aryl groups, for example, benzyl groups. The term "aralkyloxy" denotes an aralkyl group linked through an oxygen atom. The term "heteroaryl" denotes aryl groups having one or more heteroatoms contained within an aromatic ring. "Heteroaralkyl" groups are aralkyl groups which have one or more heteroatoms in their aromatic ring portion. The term "carbohydrate" includes monosaccharides, disaccharides, and polysaccharides, as well as their protected derivatives, such as, for example, mono- and diisopropylidine, and benzylidene derivatives.

As used herein, the term "amino acid" denotes a molecule containing both an amino group and a carboxyl group. As used herein the term "L-amino acid" denotes an α-amino acid having the L configuration around the α-carbon, that is, a carboxylic acid of general formula CH(COOH)(NH₂)-(sidechain), having the L-configuration. Sidechains of L-amino acids include naturally occurring and non-naturally occurring moieties. Nonnaturally occurring amino acid sidechains are moieties that are used in place of naturally occurring amino acid sidechains in, for example, amino acid analogs. See, for example, Lehninger, *Biochemistry*, Second Edition, Worth Publishers, Inc, 1975, pages 73–75. Representative α-amino acid sidechains are shown below on Table 1.

TABLE 1

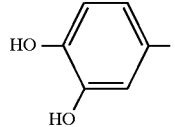

TABLE 1-continued

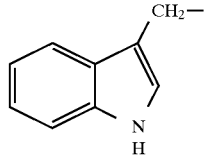

Functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other protecting groups include the phthalimido arylcarbonyls, alkylcarbonyls, alkoxycarbonyls, aryloxycarbonyls, aralkyloxycarbonyls, alkyl- and aralkylsulfonyls, and arylsulfonyl groups such as those which have the following formulas:

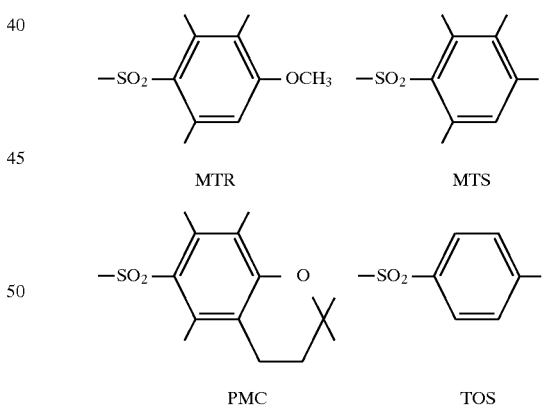

Other preferred protecting groups according to the invention may be found in Greene, T. W. and Wuts, P. G. M., *"Protective Groups in Organic Synthesis"* 2d. Ed., Wiley & Sons, 1991.

Because the ketomethylene group-containing components of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Compounds of the invention were prepared by the following procedures. $R_f$ values are reported using standard silica gel and analytical plates.

The synthesis of compounds of general Formula 1–8 are summarized in Scheme I below:

SCHEME I

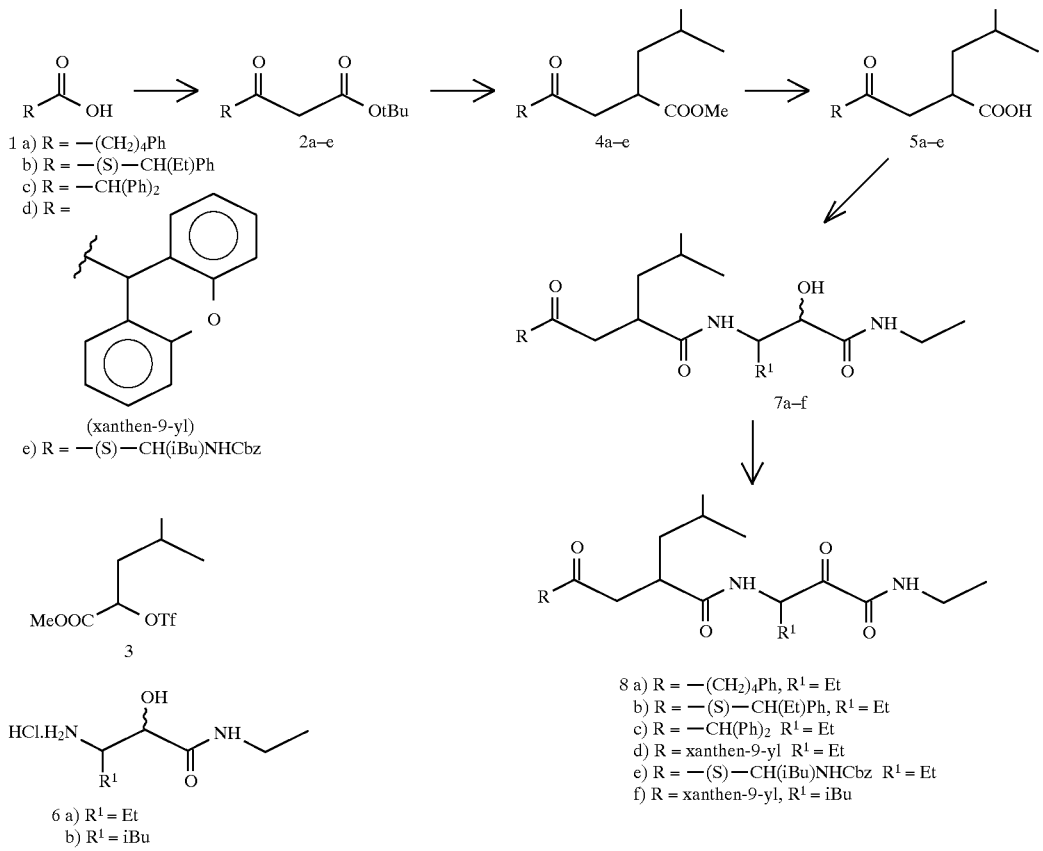

Example 1
Synthesis of Intermediates 2a–e: General Procedure

To a cooled (0° C.) solution of acid 1a–e (0.04–0.05 mole) in anhydrous tetrahydrofuran (40–50 mL) was added 1,1'-carbonyldiimidazole (1.05 eqv.). The mixture was stirred at 0° C. for 0.5 hour and then at room temperature overnight. The next morning, this solution was added slowly, over 1 hour, to a cooled (-78° C.) solution of tert-butyl lithioacetate (2.2 eqv. for 1a–d and 3.3 eqv. for 1e, generated in situ from tert-butyl acetate and lithium diisopropylamide) in tetrahydrofuran (40–50 mL) and hexane (35–40 mL). The mixture was stirred for an additional 0.5 hour and quenched with 1N HCl (2.2 eqv. for 1a–d and 3.3 eqv. for 1e), brought to 0° C. and acidified with 1N HCl to pH 3–4. The resulting aqueous solution was extracted with ethyl acetate (2×100 mL). The organic layer was washed with brine (1×40 mL), dried over anhydrous sodium sulfate, and the solvent was removed under reduced pressure.

Purification of the crude material by flash chromatography (silica gel, 5–6% ethyl acetate in hexane for 1a–d and 12% ethyl acetate in hexane for 1e) gave the desired product 2a–e in 60–70% yield. A general description of this procedure can be found in Harris, B. D. et al., *Tetrahedron Lett.* 28(25), 2837 (1987), and in Hamada, Y. et al., *J. Am. Chem. Soc.* 111, 669 (1989).

Compound 2a

Colorless oil; $R_f$ (10% ethyl acetate in hexane): 0.37; $^1$H-NMR (300 MHz, CDCl$_3$) δ7.30–7.10 (m, 5H), 3.35 (s, 2H), 2.60 (m, 2H), 2.50 (m, 2H), 1.60 (m, 4H), 1.45 (s, 9H).

Compound 2b

Colorless oil; $R_f$ (10% ethyl acetate in hexane): 0.49; $^1$H-NMR (300 MHz, CDCl$_3$) δ7.38–7.18 (m, 5H), 3.70 (t, 1H), 3.35 (d, 1H), 3.20 (d, 1H), 2.10 (m, 1H), 1.70 (m, 1H), 1.45 (s, 9H), 0.85 (t, 3H).

Compound 2c

Colorless oil; $R_f$ (10% ethyl acetate in hexane): 0.47; $^1$H-NMR (300 MHz, CDCl$_3$) δ7.40–7.20 (m, 10H), 5.35 (s, 1H), 3.45 (s, 1H), 1.45 (s, 9H).

Compound 2d

White solid, mp 101°–103° C.; $R_f$ (10% ethyl acetate in hexane): 0.46; $^1$H-NMR (300 MHz, CDCl$_3$) δ7.40–7.00 (m, 8H), 5.00 (s, 1H), 3.20 (s, 2H), 1.40 (s, 9H).

Compound 2e

Colorless oil; $R_f$ (20% ethyl acetate in hexane): 0.45; $^1$H-NMR (300 MHz, CDCl$_3$) δ7.40–7.20 (m, 5H), 5.30 (d, 1H), 5.10 (s, 2H), 4.50 (m, 1H), 3.50 (d, 1H), 3.40 (d, 1H), 1.80–1.60 (m, 2H), 1.55 (m, 1H), 1.50 (s, 9H), 1.00–0.80 (2 sets of doublet, 6H).

Example 2
Synthesis of Intermediates 4a–e: General Procedure

A solution of the keto-ester 2a–e (0.02–0.03 mole) in anhydrous tetrahydrofuran (20–25 mL) was slowly added, at room temperature, to a slurry of 60% sodium hydride in oil (1.05 eqv.) in anhydrous tetrahydrofuran (10–15 mL). After the evolution of hydrogen gas ceased, the solution was treated with 1.2–1.3 eqv. of triflate-ester 3 (generated from the corresponding (R)-hydroxyester and triflic anhydride in presence of 2,6-lutidine). The reaction mixture was stirred overnight, diluted with ether (100–150 mL), washed with water (30–40 mL), dried over magnesium sulfate and concentrated under reduced pressure to give the crude diester intermediate. This material was dissolved in trifluoroacetic acid (8–10 mL) and stirred at room temperature for 1–2 hours. Excess trifluoroacetic acid was removed and the residue was taken into benzene (30–40 mL) and heated at reflux for 1–2 hours. The solvent was removed under reduced pressure and the crude product was purified by flash chromatography (silica gel, 4–5% ethyl acetate in hexane for 2a–d and 12% ethyl acetate in hexane for 2e) to give the desired compound 4a–e in 35–45% yield over three steps. The method described above, was adapted from the procedure described in Hoffman, R. V. et al., *Tetrahedron Lett.* 34 (13), 2051 (1993), and *J. Org. Chem.* 60, 5107–5113 (1995).

4a: Colorless oil; $R_f$ (10% ethyl acetate in hexane): 0.34; $^1$H-NMR (300 MHz, CDCl$_3$) δ7.35–7.15 (m, 5H), 3.65 (s, 3H), 2.90–2.80 (m, 2H), 2.60 (m, 2H), 2.50–2.30 (m, 3H), 1.70–1.50 (m, 6H), 1.25 (m, 1H), 1.95 (d, 3H), 1.85 (d, 3H).

4b: Colorless oil; $R_f$ (10% ethyl acetate in hexane): 0.48; $^1$H-NMR (300 MHz, CDCl$_3$) δ7.40–7.18 (m, 5H), 3.60 (s, 3H), 3.50 (t, 1H), 2.85 (m, 1H), 2.75 (m, 1H), 2.45 (dd, 1H), 2.05 (m, 1H), 1.70 (m, 1H), 1.45 (m, 2H), 1.15 (m, 1H), 0.90–0.70 (m, 9H).

4c: White solid, mp 64.5°–65.5° C.; $R_f$ (10% ethyl acetate in hexane): 0.41; $^1$H-NMR (300 MHz, CDCl$_3$) δ7.40–7.15 (m, 10H), 5.15 (s, 1H), 3.65 (s, 3H), 3.00–2.85 (m, 2H), 2.60 (q, 1H), 1.50 (m, 2H), 1.20 (m, 1H), 0.90 (d, 3H), 0.80 (d, 3H).

4d: Colorless oil; $R_f$ (10% ethyl acetate in hexane): 0.40; $^1$H-NMR (300 MHz, CDCl$_3$) δ7.40–7.18 (m, 8H), 4.90 (s, 1H), 3.55 (s, 3H), 2.80–2.60 (m, 2H), 2.30 (dd, 1H), 1.30 (m, 2H), 1.00 (m,1H), 0.80 (d, 3H), 0.70 (d, 3H).

4e: Colorless oil; $R_f$ (20% ethyl acetate in hexane): 0.43; $^1$H-NMR (300 MHz, CDCl$_3$) δ7.40–7.20 (m, 5H), 5.20 (d, 1H), 5.10 (s, 2H), 4.40 (m, 1H), 3.65 (s, 3H), 3.10–2.90 (m, 2H), 2.60 (m, 1H), 1.80–1.45 (m, 4H), 1.40–1.20 (m, 2H), 1.00–0.80 (m, 12H).

Example 3

Synthesis of Intermediates 5a–e: General Procedure

A mixture of the ester 4a–e (0.005–0.006 mole), lithium hydroxide-monohydrate (1.3–1.4 eqv.), methanol (25–30 mL) and water (8–10 mL) was gently heated at 70°–75° C. for 1.5–2.0 hours. Methanol was removed under reduced pressure. The aqueous layer was washed with diethyl ether (20–25 mL), acidified at 0° C. with 1N HCl and then extracted into diethyl ether (3×20 mL). The organic layer was washed with brine (1×10 mL) and dried over anhydrous sodium sulfate. Solvent evaporation at reduced pressure yielded the intermediates 5a–e in 85–90% yield which were used without further purification.

5a: Colorless oil; $^1$H-NMR (300 MHz, CDCl$_3$) δ7.35 (m, 5H), 3.00–2.70 (m, 2H), 2.60 (q, 2H), 2.50–2.30 (m, 3H), 1.70–1.50 (m, 6H), 1.35–1.20 (m, 1H), 1.95 (d, 3H), 1.85 (d, 3H).

5b: White solid, mp 61°–63° C.; $^1$H-NMR (300 MHz, CDCl$_3$) δ7.40–7.10 (m, 5H), 3.60 (m,1H), 2.90 (m, 1H), 2.75 (m, 1H), 2.50 (m, 1H), 2.05 (m, 1H), 1.70 (m, 1H), 1.50 (m, 2H), 1.15 (m, 1H), 0.90–0.70 (m, 9H).

5c: White solid, mp 81.5°–83.5° C.; $^1$H-NMR (300 MHz, CDCl$_3$) δ7.40–7.10 (m, 10H), 5.15 (s,1H), 3.00–2.85 (m, 2H), 2.60–2.70 (m, 1H), 1.60–1.40 (m,2H), 1.30–1.20 (m, 1H), 0.90 (d, 3H), 0.80 (d, 3H).

5d: White solid, mp 125°–127° C.; $^1$H-NMR (300 MHz, CDCl$_3$) δ7.40–7.00 (m, 8H), 4.95 (s, 1H), 2.80–2.60 (m, 2H), 2.30 (dd, 1H), 1.35 (m, 2H), 1.00 (m, 1H), 0.80 (d, 3H), 0.70 (d, 3H).

5e: Colorless oil; $^1$H-NMR (300 MHz, CDCl$_3$) δ7.40–7.20 (m, 5H), 5.25 (d, 1H), 5.20–5.00 (m, 2H), 4.40–4.20 (2 sets of multiplets, 84:16, 1H), 3.00–2.80 (m, 2H), 2.65–2.50 (m, 1H), 1.80–1.50 (m, 4H), 1.45–1.20 (m, 2H), 1.00–0.80 (m,12H).

Example 4

Synthesis of Intermediates 6a–b

Compounds 6a–b were generated as a mixture of diastereomers following the procedure of Harbeson, S. L. et al. as described in *J. Med. Chem.* 37, 2918 (1994).

Example 5

Synthesis of Intermediates 7a–f: General Procedure

To a cooled (−20° C.) solution of 5a–e (0.50–1.00 mmol) in anhydrous tetrahydrofuran (3–4 mL) was added N-methylmorpholine (3.3 eqv.) followed by isobutyl chloroformate (1.1 eqv.). The mixture was stirred for 15 minutes by which time the temperature changed to 0° C. A solution of 6a–b (1 eqv.) in anhydrous N,N-dimethylformamide (3–4 mL) was added to the reaction mixture. The cooling bath was removed and the mixture was stirred for another 2 hours. The resulting mixture was then poured into water (5–8 mL) and extracted into ethyl acetate (3×15 mL). The organic layer was washed with 2% citric acid solution (2×5 mL), saturated sodium bicarbonate solution (2×5 mL), brine (1×5 mL) and dried over anhydrous sodium sulfate. Solvent evaporation under reduced pressure gave a crude material which was purified by flash chromatography (silica gel, 2–3% methanol-methylene chloride) to produce 7a–f as diastereomeric mixtures (at hydroxy center) in 25–30% yield.

7a: Diastereomers; white solid, mp 97°–99° C.; $R_f$ (5% methanol in methylene chloride): 0.47; $^1$H-NMR (300 MHz, CDCl$_3$) δ7.30–7.10 (m, 5H), 6.95–6.80 (broad, 1H), 6.30 (d, 1H), 5.80–5.50 (broad, 1H), 4.15 (s, 1H), 3.90–3.80 (m, 1H), 3.40–3.10 (m, 2H), 2.90–2.70 (m 2H), 2.65–2.55 (broad, 2H), 2.45–2.35 (m, 3H), 2.00–1.70 (m 2H), 1.65–1.40 (m, 7H), 1.20–1.00 (t, 3H), 0.95–0.75 (m, 9H).

7b: Separated diastereomers

The faster moving isomer was a white solid, mp 150°–160° C. (softening to melt); $R_f$ (5% methanol in methylene chloride): 0.37; $^1$H-NMR (300 MHz, CDCl$_3$) δ7.40–7.10 (m, 5H), 7.00–6.80 (m, 1H), 6.80–6.70 (m, 1H), 4.30–3.60 (m, 3H), 3.60–3.50 (m, 1H), 3.40–3.20 (m, 3H), 2.80–2.60 (m, 2H), 2.60–2.40 (m, 1H), 2.10–1.90 (m, 2H), 1.80–1.60 (m, 2H), 1.50–1.30 (m, 2H), 1.25–1.10 (m, 3H), 1.00–0.70 (m, 12H);

The slower moving isomer was a white solid, mp 115°–130° C. (softening to melt); $R_f$ (5% methanol in methylene chloride): 0.35; $^1$H-NMR (300 MHz, CDCl$_3$) δ7.40–7.10 (m, 5H), 7.00–6.80 (m, 1H), 6.80–6.70 (m, 1H), 4.30–3.60 (m, 3H), 3.60–3.50 (m, 1H), 3.40–3.20 (m, 3H), 2.80–2.60 (m, 2H), 2.60–2.40 (m, 1H), 2.10–1.90 (m, 2H), 1.80–1.60 (m, 2H), 1.50–1.30 (m, 2H), 1.25–1.10 (m, 3H), 1.00–0.70 (m, 12H).

7c: Separated diastereomers

The faster moving isomer was a white solid, mp 134°–154° C. (softening to melt); $R_f$ (5% methanol in methylene chloride): 0.44; $^1$H-NMR (300 MHz, CDCl$_3$) δ7.40–7.10 (m, 10H), 6.95–6.85 (broad, 1H), 6.20 (d, 1H), 5.75–5.55 (broad, 1H), 5.10 (s, 1H), 4.15 (s, 1H), 3.90–3.75 (m, 1H), 3.40–3.25 (m, 1H), 3.20–3.05 (m, 1H), 3.05–2.95 (dd, 1H), 2.85–2.70 (m, 1H), 2.65–2.50 (dd, 1H), 1.90–1.60 (m, 3H), 1.60–1.40 (m, 2H), 1.20–1.05 (t, 3H), 1.00–0.75 (m, 9H);

The slower moving isomer was a white solid, mp 124°–144° C. (softening to melt); $R_f$ (5% methanol in methylene chloride): 0.38; $^1$H-NMR (300 MHz, CDCl$_3$) δ7.40–7.10 (m, 10H), 6.95–6.85 (broad, 1H), 6.20 (d, 1H), 5.75–5.55 (broad, 1H), 5.10 (s, 1H), 4.15 (s, 1H), 3.90–3.75 (m, 1H), 3.40–3.25 (m, 1H), 3.20–3.05 (m, 1H), 3.05–2.95 (dd, 1H), 2.85–2.70 (m, 1H), 2.65–2.50 (dd, 1H), 1.90–1.60 (m, 3H), 1.60–1.40 (m, 2H), 1.20–1.05 (t, 3H), 1.00–0.75 (m, 9H).

7d: Diastereomeric: white solid, mp 185°–195° C. (softening to melt); $R_f$(5% methanol in methylene chloride): 0.46; $^1$H-NMR (300 MHz, CDCl$_3$) δ7.40–7.00 (m, 8H), 6.90–6.80 and 6.70–6.60 (2 sets of m, 1:1, 1H), 6.25 and 6.00 (2 sets of d, 1H), 5.65–5.55 and 5.40–5.30 (2 sets of m, 1:1, 1H), 4.90 (s, 1H), 4.10 (d, 1H), 3.80–3.60 (m, 1H), 3.40–3.00 (m, 2H), 2.70–2.40 (m, 2H), 2.40–2.20 (dt, 1H), 1.80–1.40 (m, 3H), 1.40–1.20 (m, 2H), 1.15–1.00 (m, 3H), 1.00–0.80 (m, 3H), 0.80–0.60 (m, 6H).

7e: Diastereomeric: white solid, mp 115°–125° C. (softening to melt); $R_f$ (5% methanol in methylene chloride): 0.47; $^1$H-NMR (300 MHz, CDCl$_3$) δ7.40–7.20 (m, 5H), 6.95–6.85 (broad, 1H), 6.30–6.20 (m, 1H), 5.30–5.10 (m, 2H), 5.05 (d, 2H), 4.40–4.20 (m, 1H), 4.00–3.80 (m, 1H), 3.35–3.10 (m, 2H), 3.00–2.70 (m, 2H), 2.55–2.40 (m, 1H), 2.00–1.20 (m, 9H), 1.15–1.05 (t, 3H), 1.00–0.70 (m, 15H).

7f: Diastereomeric: white solid, mp 196°–201° C. (softening to melt); $R_f$ (5% methanol in methylene chloride): 0.47; $^1$H-NMR (300 MHz, CDCl$_3$) δ7.40–7.00 (m, 8H), 6.95–6.85 (broad, 1H), 6.05 (d, 1H), 5.35 (d, 1H), 4.90 (s, 1H), 4.05 (d, 1H), 4.00–3.90 (m, 1H), 3.40–3.20 (m, 1H), 3.20–3.10 (m, 1H), 2.65–2.60 (dd, 1H), 2.60–2.45 (m, 1H), 2.30–2.20 (dd, 1H), 1.90–1.70 (m, 2H), 1.70–1.50 (m, 1H), 1.45–1.20 (m, 3H), 1.15 (t, 3H), 0.95 (d, 3H), 0.85 (d, 3H), 0.80 (d, 3H), 0.70 (d, 3H).

Example 6
Synthesis of Ketoamides 8a–f: General Procedure

To a cooled (0° C.) solution of 7a–f (0.05–0.10 mmol) in anhydrous methylene chloride (2–3 mL) was added Dess-Martin periodinane reagent (3.00–4.00 eqv.). The cooling bath was removed and the mixture was stirred for an additional 30–45 minutes. It was then diluted with methylene chloride (10–15 mL) and washed with 10% sodium thiosulfate solution (5×5 mL), saturated sodium bicarbonate solution (2×5 mL) and brine (1×5 mL). Drying over anhydrous sodium sulfate and solvent removal under reduced pressure gave a material which was washed with n-pentane (5–8 mL) and dried under vacuum to generate the desired target 8a–f in 50–60% yield. A general description of the procedure can be found in Patel, D. V. et al., *J. Med. Chem.* 36, 2431–2447 (1993).

8a: White solid, mp 123°–124° C.; $R_f$ (5% methanol in methylene chloride): 0.50; $^1$H-NMR (300 MHz, CDCl$_3$) δ7.30–7.10 (m, 5H), 6.95–6.80 (broad, 1H), 6.30 (d, 1H), 5.30–5.10 (m, 1H), 3.40–3.30 (m, 2H), 2.90–2.70 (m 2H), 2.65–2.55 (broad, 2H), 2.45–2.35 (m, 3H), 2.10–1.90 (m 1H), 1.75–1.40 (m, 8H), 1.30–1.00 (m, 3H), 0.95–0.75 (m, 9H).

8b: White solid, mp 105°–115° C. (softening to melt); $R_f$ (5% methanol in methylene chloride): 0.53; $^1$H-NMR (300 MHz, CDCl$_3$) δ7.40–7.10 (m, 5H), 7.00–6.80 (broad, 1H), 6.35–6.20 (m, 1H), 5.35–5.20 (m, 1H), 5.20–5.00 (m, 1H), 3.60–3.50 (m, 1H), 3.40–3.20 (m, 3H), 2.90–2.70 (m, 2H), 2.40 (dt, 1H), 2.10–1.90 (m, 2H), 1.80–1.60 (m, 2H), 1.50–1.30 (m, 1H), 1.25–1.10 (m, 3H), 1.00–0.70 (m, 12H).

8c: White solid, mp 145°–146° C.; $R_f$ (5% methanol in methylene chloride): 0.62; $^1$H-NMR (300 MHz, CDCl$_3$) δ7.40–7.10 (m, 10H), 6.90–6.75 (broad, 1H), 6.25 (d, 1H), 5.25–5.15 (m, 1H), 5.10 (s, 1H), 3.40–3.25 (m, 2H), 3.05–2.95 (dd, 1H), 2.80 (m, 1H), 2.65–2.50 (dd, 1H), 2.00 (m, 1H), 1.70–1.40 (m, 4H), 1.35–1.05 (m, 3H), 1.00–0.75 (m, 9H).

8d: White solid, mp 184°–185° C.; $R_f$ (5% methanol in methylene chloride): 0.50; $^1$H-NMR (300 MHz, CDCl$_3$) δ7.40–7.00 (m, 8H), 6.85–6.75 (broad, 1H), 6.15 (d, 1H), 5.20–5.10 (m, 1H), 4.90 (s, 1H), 3.40–3.25 (m, 2H), 2.75–2.65 (dd, 1H), 2.60–2.50 (m, 1H), 2.40–2.25 (dd, 1H), 2.00 (m, 1H), 1.70–1.55 (m, 2H), 1.40–1.20 (m, 2H), 1.15 (t, 3H), 0.90 (t, 3H), 0.80 (d, 3H), 0.70 (d, 3H).

8e: White solid, mp 157°–158° C.; $R_f$ (5% methanol in methylene chloride): 0.50; $^1$H-NMR (300 MHz, CDCl$_3$) δ7.40–7.20 (m, 5H), 6.85–6.75 (broad, 1H), 6.20 (m, 1H), 5.30–5.10 (m, 2H), 5.00 (d, 2H), 4.40–4.00 (m, 1H), 3.35–3.20 (m, 1H), 3.00–2.80 (m, 1H), 2.80–2.60 (m, 1H), 2.55–2.35 (m, 1H), 2.00–1.85 (m, 1H), 1.70–1.20 (m, 8H), 1.15–1.05 (m, 3H), 1.00–0.70 (m, 15H).

8f: White solid, mp 182°–183° C.; $R_f$ (5% methanol in methylene chloride): 0.70; $^1$H-NMR (300 MHz, CDCl$_3$) δ7.40–7.00 (m, 8H), 6.85–6.75 (broad, 1H), 6.15 (d, 1H), 5.25–5.15 (m, 1H), 4.90 (s, 1H), 3.40–3.25 (m, 2H), 2.75–2.65 (dd, 1H), 2.60–2.50 (m, 1H), 2.40–2.25 (dd, 1H), 1.80–1.60 (m, 4H), 1.45–1.20 (m, 2H), 1.15 (t, 3H), 0.90 (t, 6H), 0.80 (d, 3H), 0.70 (d, 3H).

The synthesis of compounds of general Formula 9–14 are summarized in Scheme II below:

SCHEME II

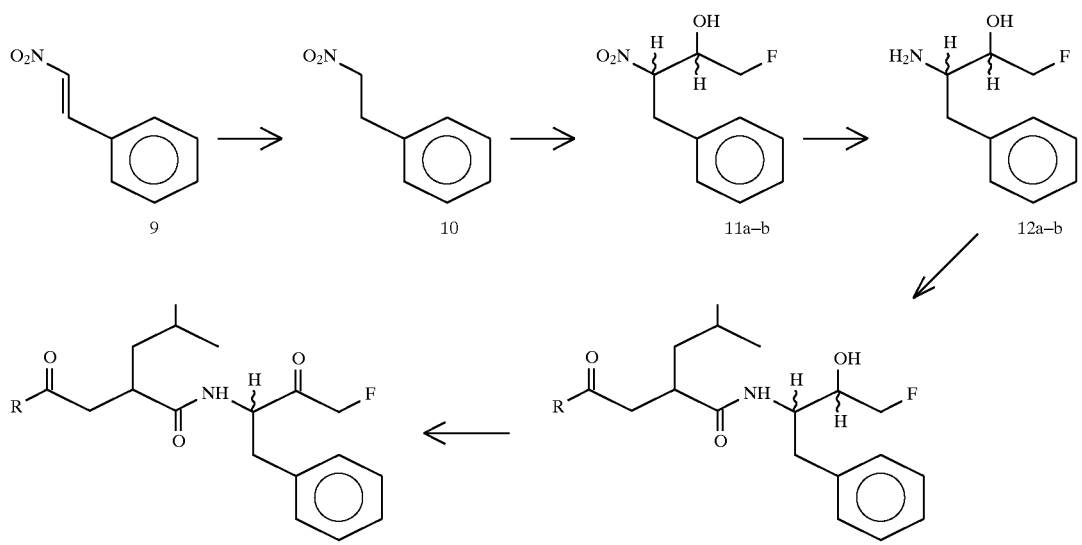

14 a) R = —(S)—CH(Et)Ph
b) R = xanthen-9-yl
c) R = —(S)—CH(iBu)NHCbz

Example 7

Synthesis of Intermediate 10

To a stirring mixture of trans-β-nitrostyrene (9, 5.25 g, 0.035 mol) and silica gel (10 g, 230–400 mesh) in chloroform (400 mL) and isopropanol (75 mL) at room temperature, was slowly added sodium borohydride (5.50 g, 0.145 mol) over a period of 45 minutes. The reaction mixture was stirred for an additional 15 minutes and then carefully quenched with 10% hydrochloric acid (20 mL). Separated solid was filtered and washed with chloroform (50 mL). Combined filtrate and washing was washed with water (1× 20 mL), brine (1×20 mL) and dried over anhydrous sodium sulfate. Solvent evaporation at reduced pressure gave a crude material which was purified by flash chromatography (silica gel, 8% ethyl acetate-hexane) to give 2.86 g of compound 10.

10: Colorless oil (spicy odor); $R_f$ (10% ethyl acetate in hexane): 0.40; $^1$H-NMR (300 MHz, CDCl$_3$) δ7.40–7.20 (m, 5H), 4.60 (t, 2H), 3.30 (t, 2H).

Example 8

Synthesis of Intermediates 11a–b

To a cooled (−78° C.) solution of oxalyl chloride (2M) in methylene chloride (11.60 mL, 0.0232 mol) was added slowly dimethyl sulfoxide (3.65 g, 3.32 mL, 0.0467 mol). The reaction mixture was stirred for 15 minutes. A solution of 2-fluoroethanol (1.16 g, 0.0181 mol) in methylene chloride (10 mL) was then slowly introduced into the reaction flask. After stirring for another 15 minutes, the reaction mixture was diluted with anhydrous methylene chloride (180 mL) and triethylamine (9.20 g, 12.63 mL, 0.090 mol) was added to it. Stirring was continued for another 2 hours by which time temperature changed to room temperature. At this time, a solution of compound 10 (2.74 g, 0.0181 mol) in anhydrous methylene chloride (10 mL) was added to the reaction mixture and stirring was continued overnight. The mixture was then washed with water (1×30 mL), 4% hydrochloric acid (3×20 mL), water (1×20 mL), saturated sodium bicarbonate solution (2×20 mL) and brine (1×20 mL). Drying over anhydrous sodium sulfate and solvent evaporation gave a crude material which was purified by flash chromatography (silica gel, 25% ethyl acetate-hexane) to give 11a and 11b as erythro/threo isomers. Combined yield was 3.01 g. A general description of this procedure can be found in Imperiali, B. et al., *Tetrahedron Lett.* 27(2), 135, 1986 and in Revesz, L. et al., *Tetrahedron Lett.* 35(52), 9693, 1994.

11a: White solid, mp 71°–73° C.; $R_f$(30% ethyl acetate in hexane): 0.46; $^1$H-NMR (300 MHz, CDCl$_3$) δ7.40–7.10 (m, 5H), 4.90 (m, 1H), 4.60 (m, 1H), 4.50–4.30 (m, 2H), 3.45–3.25 (m, 2H), 2.70 (d, 1H).

11b: Colorless oil; $R_f$(30% ethyl acetate in hexane): 0.42; $^1$H-NMR (300 MHz, CDCl$_3$) δ7.40–7.15 (m, 5H), 4.90 (m, 1H), 4.65 (m,1H), 4.50 (m, 1H), 4.20 (m, 1H), 3.40–3.30 (m, 2H), 2.90 (d,1H).

Example 9

Synthesis of Intermediates 12a–b

A mixture of intermediate 11a (0.48 g, 2.25 mmol), absolute ethanol (20 mL) and Raney-Nickel (catalytic) was hydrogenated (60 psi) in a Parr apparatus for 5 hours. Filtration through a celite pad and solvent evaporation gave 0.41 g of 12a which was used without further purification. Similar treatment of 11b (0.80 g, 3.75 mmol) gave 0.51 g of 12b.

12a: White solid, mp 64°–67° C.; $^1$H-NMR (300 MHz, CDCl$_3$) δ7.40–7.10 (m, 5H), 4.70 (d, 1H), 4.50 (d, 1H), 3.90–3.70 (m, 1H), 3.30–3.10 (m, 1H), 2.95 (dd, 1H), 2.60–2.45 (q, 1H), 2.20–1.70 (broad, 3H).

12b: White solid, mp 67°–70° C.; $^1$H-NMR (300 MHz, CDCl$_3$) δ7.40–7.10 (m, 5H), 4.70 (d, 1H), 4.55 (d, 1H), 3.70–3.50 (m, 1H), 3.20–3.00 (m, 1H), 2.95 (dd, 1H), 2.60–2.45 (q, 1H), 2.20–1.65 (broad, 3H).

Example 10

Synthesis of Intermediates 13a–c

These intermediates were generated as diastereomeric mixtures following the same synthetic procedure as described for the syntheses of the compounds 7a–f. Thus, the coupling of 0.32 g of 5b with 0.22 g of 12b produced 0.30 g of 13a. Similarly, 0.34 g of 5d and 0.36 g of 5e yielded 0.14 g and 0.25 g of 13b and 13c respectively.

13a: Viscous oil; $R_f$(5% methanol in methylene chloride): 0.62; $^1$H-NMR (300 MHz, CDCl$_3$) δ7.30–7.00 (m, 10H), 6.10–5.80 (2 sets of d, 1H), 4.40–3.70 (m, 5H), 3.50–3.30 (m, 1H), 3.00–2.20 (m, 5H), 2.00–1.90 (m, 1H), 1.70–1.50 (m, 1H), 1.30–1.15 (m, 2H), 1.00–0.60 (m, 9H).

13b: White solid, mp 150°–155° C. (softening to melt); $R_f$ (5% methanol in methylene chloride): 0.47; $^1$H-NMR (300 MHz, CDCl$_3$) δ7.40–6.95 (m, 13H), 5.85–5.65 (2 sets of d, 1H), 4.80 (d, 1H), 4.60–4.20 (m 3H), 4.10–3.75 (m, 2H), 3.10–2.60 (m, 3H), 2.50–2.15(m, 2H), 1.30–1.10 (m, 1H), 1.00–0.75 (m, 2H), 0.70–0.50 (m, 6H).

13c: Viscous oil; $R_f$(5% methanol in methylene chloride): 0.51; $^1$H-NMR (300 MHz, CDCl$_3$) δ7.40–7.15 (m, 10H), 6.30–6.00 (m, 1H), 5.35–5.20 (m, 1H), 5.10 (q, 1H), 4.50–4.15 (m, 4H), 4.10–3.80 (m, 2H), 3.00–2.40 (m, 5H), 1.80–1.00 (m, 6H), 1.00–0.70 (m, 12H).

Example 11

Synthesis of Fluoroketones 14a–c

These compounds were generated as diastereomeric mixtures following the same synthetic procedure as described for the syntheses of the compounds 8a–f. Thus, the oxidation of 0.055 g of 13a produced 0.028 g of 14a. Similarly, 0.027 g of 13b and 0.040 g of 13c yielded 0.020 g and 0.023 g of 14b and 14c respectively.

14a: Viscous oil; $R_f$ (30% ethyl acetate in hexane): 0.45; $^1$H-NMR (300 MHz, CDCl$_3$) δ7.40–7.00 (m, 10H), 6.25–6.00 (2 sets of m, 1H), 5.10–4.55 (m, 3H), 3.50–3.40 (m, 1H), 3.20–2.90 (m, 2H), 2.80–2.50 (m, 2H), 2.45–2.25 (m, 1H), 2.10–1.90 (m, 1H), 1.80–1.60 (m, 2H), 1.50–1.20 (m, 2H), 1.00–0.60 (m, 9H).

14b: White solid, mp 144°–150° C. (softening to melt); $R_f$ (30% ethyl acetate in hexane): 0.40; $^1$H-NMR (300 MHz, CDCl$_3$) δ7.30–6.95 (m, 13H), 6.05–5.85 (2 sets of d, 1H), 5.00–4.45 (m 4H), 3.10–2.80 (m, 2H), 2.60–2.15(m, 3H), 1.30–1.10 (m, 1H), 1.00–0.75 (m, 2H), 0.70–0.50 (m, 6H).

14c: Viscous oil; $R_f$ (30% ethyl acetate in hexane): 0.33; $^1$H-NMR (300 MHz, CDCl$_3$) δ7.40–7.10 (m, 10H), 6.25–6.05 (m, 1H), 5.20–4.60 (m, 6H), 4.40–4.20 (m, 1H), 3.20–2.40 (m, 5H), 1.80–1.00 (m, 6H), 1.00–0.70 (m, 12H).

The synthesis of compounds of general Formula 15 and 16 are summarized in Scheme III below:

SCHEME III

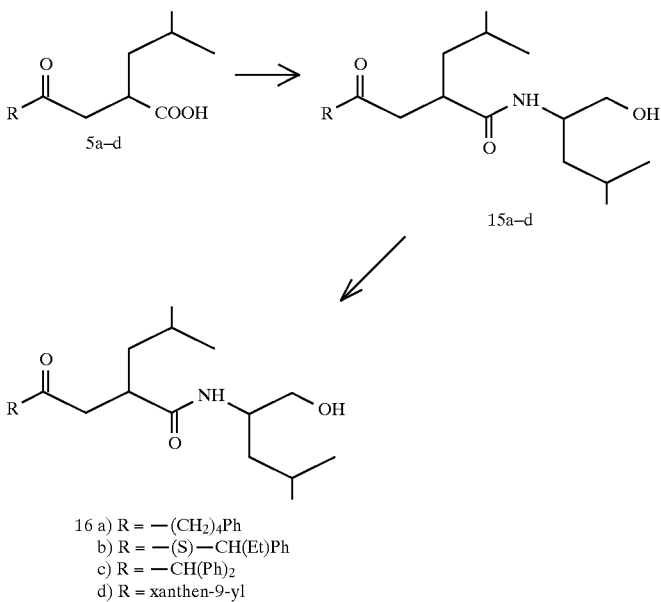

16 a) R = —(CH₂)₄Ph
   b) R = —(S)—CH(Et)Ph
   c) R = —CH(Ph)₂
   d) R = xanthen-9-yl

Example 12
Synthesis of Intermediates 15a–d: General Procedure

To a cooled (0° C.) solution of 5a–d (0.0005–0.001 mol) in anhydrous N,N-dimethylformamide (3–4 mL) was added N-methylmorpholine (3 eqv.) followed by 1-HOBt (1 eqv.) and BOP (1 eqv.). The mixture was stirred for 15 minutes and to it was added (S)-leucinol (1.3–1.4 eqv.). The cooling bath was removed and the mixture was stirred overnight, poured into water (5 mL) and extracted into ethyl acetate (3×10 mL). The organic layer was washed with 2% citric acid solution (2×5 mL), saturated sodium bicarbonate solution (2×5 mL), brine (1×5 mL) and dried over anhydrous sodium sulfate. Solvent evaporation under reduced pressure gave a crude material which was purified by flash chromatography (silica gel, 4–5% methanol-methylene chloride) to produce 15a–d in 40–60% yield.

15a: Viscous oil; $R_f$ (5% methanol in methylene chloride): 0.40; $^1$H-NMR (300 MHz, CDCl₃) δ7.40–7.10 (m, 5H), 5.85 (d, 1H), 3.85 (m, 1H), 3.60 (m, 1H), 3.50 (m, 1H), 3.00–2.80 (m, 2H), 2.70 (m, 1H), 2.60 (m, 2H), 2.50–2.30 (m, 3H), 1.70–1.50 (m, 8H), 1.45–1.20 (m, 2H), 1.00–0.80 (m, 12H).

15b: White gum; $R_f$ (5% methanol in methylene chloride): 0.36; $^1$H-NMR (300 MHz, CDCl₃) δ7.40–7.10 (m, 5H), 5.85 (m, 1H), 4.00–3.80 (m, 1H), 3.70–3.40 (m, 3H), 3.00–2.70 (m, 2H), 2.50–2.30 (td, 1H), 2.00 (m, 1H), 1.80–1.20 (m, 8H), 1.00–0.70 (m, 15H).

15c: White solid, mp 110°–112° C.; $R_f$ (5% methanol in methylene chloride): 0.45; $^1$H-NMR (300 MHz, CDCl₃) δ7.40–7.10 (m, 10H), 5.85 (d, 1H), 5.10 (s, 1H), 3.85 (m, 1H), 3.60 (m, 1H), 3.50 (m, 1H), 3.00 (q, 1H), 2.80–2.70 (m, 2H), 2.30 (dd, 1H), 1.60–1.00 (m, 6H), 1.00–0.80 (m, 12H).

15d: White solid, mp 168°–169° C.; $R_f$ (5% methanol in methylene chloride): 0.55; $^1$H-NMR (300 MHz, CDCl₃) δ7.40–7.00 (m, 8H), 5.70 (d, 1H), 4.90 (s, 1H), 3.85 (m, 1H), 3.60 (m, 1H), 3.50 (m, 1H), 2.80 (t, 1H), 2.70 (q, 1H), 2.50 (m, 1H), 2.30 (dd, 1H), 1.60 (m, 1H), 1.50–1.20 (m, 5H), 1.00–0.60 (4 sets of doublets, 12H).

Example 13
Synthesis of Aldehydes 16a–d: General Procedure

To a cooled (0° C.) solution of alcohol 15a–d (0.05–0.10 mmol) in anhydrous methylene chloride (2–3 mL) and anhydrous dimethyl sulfoxide (2–3 mL) was added triethylamine (3.00 eqv.). Sulfur trioxide-pyridine complex (3.00 eqv.) was slowly added to the stirred mixture over a period of 5 minutes and the ice-bath was removed. The mixture was stirred for another 1 hour, poured into water (10 mL) and extracted into ether (3×10 mL). The organic layer was washed with 2% citric acid solution (2×5 mL), saturated sodium bicarbonate solution (2×5 mL), brine (1×5 mL) and dried over anhydrous magnesium sulfate. Solvent evaporation gave a residue which was washed with n-pentane (5–8 mL) and dried under vacuum to produce the desired compound 16a–d in 50–60% yield. A general description of this procedure can be found in Luly, J. R. et al., J. Org. Chem. 52, 1487–1492 (1987).

16a: White solid, mp 64°–65° C.; $R_f$ (30% ethyl acetate in hexane): 0.48; $^1$H-NMR (300 MHz, CDCl₃) δ9.55 (s, 1H), 7.30–7.10 (m, 5H), 6.10 (d, 1H), 4.50 (m, 1H), 3.00–2.80 (m, 2H), 2.60 (m, 2H), 2.40 (m, 3H), 1.80–1.60 (m, 8H), 1.50–1.10 (m, 2H), 1.00–0.80 (m, 12H).

16b: Viscous liquid: $R_f$ (30% ethyl acetate in hexane): 0.52; $^1$H-NMR (300 MHz, CDCl₃) δ9.55 and 9.45 (2 singlets, 3:2, 1H), 7.40–7.10 (m, 5H), 6.10 (m, 1H), 4.60–4.30 (2 sets of multiplate, 3:2, 1H), 3.50 (t, 1H), 3.00–2.70 (m, 2H), 2.50–2.30 (td, 1H), 2.00 (m, 1H), 1.80–1.20 (m, 7H), 1.00–0.70 (m, 15H).

16c: White solid, mp 85°–95° C. (softening to melt); $R_f$ (30% ethyl acetate in hexane): 0.45; $^1$H-NMR (300 MHz, CDCl₃) δ9.55 (s, 1H), 7.40–7.10 (m, 10H), 6.10 (d, 1H), 5.10 (s, 1H), 4.50 (m, 1H), 3.00 (q, 1H), 2.90–2.70 (m, 1H), 2.60 (dd, 1H), 1.80–1.00 (m, 6H), 1.00–0.80 (m, 12H).

16d: White solid, mp 115°–125° C. (softening to melt); $R_f$ (30% ethyl acetate in hexane): 0.45; $^1$H-NMR (300 MHz, CDCl₃) δ9.50 (s, 1H), 7.40–7.00 (m, 8H), 6.00 (d, 1H), 4.90 (s, 1H), 4.40 (m, 1H), 2.80–2.65 (q, 1H), 2.60 (m, 1H), 2.30 (dd, 1H), 1.80–1.20 (m, 6H), 1.00–0.60 (4 sets of doublets, 12H).

The synthesis of compounds 16f–g, and of general Formula 17–23, are summarized in Scheme IV below:

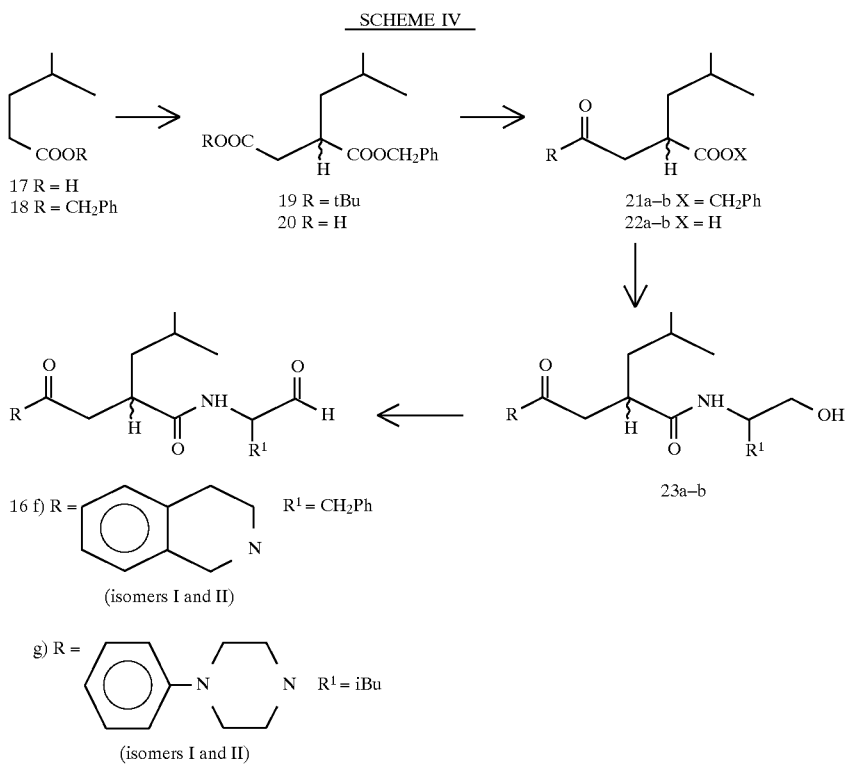

Example 14
Synthesis of Intermediate 18

A mixture of 4-methylvaleric acid (17, 12.31 g, 0.106 mol), benzyl alcohol (10.88 g, 0.10 mol) and p-toluenesulfonic acid monohydrate (1.00 g) in benzene (100 mL) was refluxed using a Dean-Stark water separator for 2 hours. After cooling, benzene was removed and the mixture was diluted with ether (50 mL), washed successively with saturated NaHCO$_3$ solution (2×20 mL), brine (1×20 mL), dried (MgSO$_4$), and concentrated to give the compound 18 (20.00 g).

18: Colorless oil; R$_f$ (5% ethyl acetate in hexane): 0.46; $^1$H-NMR (300 MHz, CDCl$_3$) δ7.40–7.20 (m, 5H), 5.10 (s, 2H), 2.35 (t, 2H), 1.55 (m, 3H), 0.90 (d, 6H).

Example 15
Synthesis of Intermediate 19

To a cooled (–78° C.) solution of lithium diisopropylamide (12 mmol) in a mixture of tetrahydrofuran (20 mL) and hexane (4.8 mL) (obtained in situ from diisopropylamine and n-butyllithium) was added slowly the compound 18 (2.06 g, 10 mmol) in anhydrous tetrahydrofuran (8 mL). The mixture was stirred for 30 minutes and tert-butyl bromoacetate (2.34 g, 12 mol) in hexamethylphosphoramide (2.09 mL) was added to the flask. The mixture was stirred at –78° C. for 30 minutes, slowly brought to 0° C. over a period of 2 h and quenched by the cautious addition of saturated ammonium chloride (50 mL). The mixture was extracted into ether (3×50 mL) and the combined organic layer was washed with brine (1×25 mL), dried over anhydrous MgSO$_4$ and concentrated to give a crude material. Purification of this material by flash chromatography over silica using 2% ethyl acetate in hexane as an eluant gave 2.00 g of racemic diester 19.

19: Colorless oil; R$_f$ (5% ethyl acetate in hexane): 0.34; $^1$H-NMR (300 MHz, CDCl$_3$) δ7.40–7.30 (m, 5H), 5.15 (q, 2H), 2.90 (m, 1H), 2.60 (q, 1H), 2.35 (q, 1H), 1.60–1.20 (m, 3H), 1.40 (s, 9H), 1.00–0.80 (2 sets of d, 6H).

Example 16
Synthesis of Intermediate 20

A mixture of diester 19 (0.54 g, 1.673 mmol) and 90% trifluoroacetic acid (1.5 mL) in methylene chloride (3 mL) was stirred at room temperature for 1.5 hours. Solvent and excess reagent were removed under reduced pressure to give 0.44 g of a crude product. An $^1$H-NMR (CDCl$_3$) of this crude product showed no detectable peak for the tert-butyl ester moiety at δ1.40. This material was used without further purification.

Example 17
Synthesis of Intermediates 21a–b

To a stirred mixture of 20 (0.95 g, 3.60 mmol) and 1,2,3,4-tetrahydroisoquinoline (0.48 g, 3.60 mmol) in anhydrous methylene chloride (8 mL) at room temperature, was added triethylamine (0.80 g, 7.92 mmol) followed by BOP-Cl (0.92 g, 3.60 mmol). The mixture was stirred overnight, diluted with methylene chloride (10 mL) and washed successively with water (1×5 mL), saturated NaHCO$_3$ (2×5 mL) and brine (1×5 mL). Drying over Na$_2$SO$_4$ and solvent evaporation gave a crude material which was purified by flash chromatography over silica using 20% ethyl acetate in hexane to give 0.89 g of racemic 21a.

Similar treatment of Compound 20 (0.44 g, 1.67 mmol) with 0.27 g of 1-phenylpiperazine yielded 0.45 g of racemic Compound 21b. A general description of this procedure can be found in Tung, R. D. et al., J. Am. Chem. Soc. 107, 4342–4343 (1985).

21a: Colorless oil; R$_f$ (20% ethyl acetate in hexane): 0.70; $^1$H-NMR (300 MHz, CDCl$_3$) δ7.40–7.00 (m, 9H), 5.10 (q, 2H), 4.70 (q, 2H), 3.90–3.60 (m, 2H), 3.20–3.00 (m 1H), 2.90–2.70 (m, 3H), 2.50–2.40 (m, 1H), 1.70–1.50 (m, 2H), 1.40–1.30 (m, 1H), 1.00–0.80 (m, 6H).

21b: White solid, mp 90°–105° C. (softening to melt); $R_f$ (30% ethyl acetate in hexane): 0.31; $^1$H-NMR (300 MHz, CDCl$_3$) δ7.40–7.20 (m, 7H), 7.00–6.90 (t, 3H), 5.20–5.00 (q, 2H) 3.80–3.55 (m, 4H), 3.20–3.00 (m, 5H), 2.80 (q, 1H), 2.40 (dd, 1H), 1.60 (m, 2H), 1.30 (m, 1H), 1.00–0.80 (2 sets of d, 6H).

Example 18
Synthesis of Intermediates 22a–b

A mixture of the benzyl ester 21a (0.88 g, 2.32 mmol) and 10% Pd-C (0.30 g, Degussa, H$_2$O content 50%) in methanol (30 mL) was hydrogenated for 2 hours in a Parr apparatus (40–30 psi). The reaction mixture was filtered through a celite pad and concentrated to give 0.67 g of the racemic acid 22a.

Similar treatment of 0.30 g of 21b produced 0.23 g of racemic acid 22b.

22a: Pale yellow solid, mp 95°–105° C. (softening to melt); $^1$H-NMR (300 MHz, CDCl$_3$) δ7.40–7.00 (m, 4H), 5.00–4.80 (q, 2H), 4.00–3.60 (m, 2H), 3.20–3.00 (m 1H), 2.90–2.70 (m, 3H), 2.60–2.40 (m, 1H), 1.80–1.60 (m, 2H), 1.40–1.30 (m, 1H), 1.00–0.80 (m, 6H).

22b: Pale yellow oil; $^1$H-NMR (300 MHz, CDCl$_3$) δ7.40–7.20 (m, 2H), 7.00–6.90 (t, 3H), 3.80–3.55 (m, 4H), 3.20–3.10 (m, 4H), 3.00 (m, 1H), 2.80 (q, 1H), 2.50 (dd, 1H), 1.60 (m, 1H), 1.30 (m, 2H), 1.00–0.80 (m, 6H).

Example 19
Synthesis of Intermediates 23a–b

These compounds were generated as separated diastereomeric mixtures following the same synthetic procedures as described for the syntheses of the compounds 15a–e. Thus 0.23 g of 22a generated 0.20 g of 23a and 0.32 g of 22b produced 0.22 g of 23b.

23a: Isomer I: White gum, $R_f$ (ethyl acetate): 0.62; $^1$H-NMR (300 MHz, CDCl$_3$) δ7.30–7.10 (m, 9H), 6.60 (d, 1H), 4.70–4.50 (q, 2H), 4.50 (s, 1H), 4.00 (m, 1H), 3.90–3.50 (m, 4H), 3.00–2.60 (m, 6H), 2.40–2.30 (m, 1H), 1.70–1.60 (m, 1H), 1.60–1.40 (m, 1H), 1.20 (m, 1H), 1.00–0.80 (m, 6H).

23a: Isomer II: White gum; $R_f$ (ethyl acetate): 0.44; $^1$H-NMR (300 MHz, CDCl$_3$) δ7.30–7.00 (m, 9H), 6.00 (m, 1H), 4.8–4.50 (q, 2H), 4.60 (s, 1H), 4.30 (m, 1H), 3.90–3.40 (m, 4H), 3.00–2.60 (m, 6H), 2.40–2.20 (m, 1H), 1.60–1.50 (m, 1H), 1.30–1.20 (m, 1H), 1.00 (m, 1H), 0.80–0.60 (m, 6H).

23b: Isomer I: Viscous oil; $R_f$ (70% ethyl acetate in hexane): 0.28; $^1$H-NMR (300 MHz, CDCl$_3$) δ7.30–7.20 (t, 2H), 7.00–6.90 (t, 3H), 6.25 (d, 1H),3.90 (m, 1H), 3.70 (m, 2H), 3.60 (m, 4H), 3.20–3.10 (m, 5H), 2.90 (m, 1H), 2.80 (q, 1H), 2.40 (dd, 1H), 1.80–1.20(m, 6H), 1.00–0.80 (m, 12H).

23b: Isomer II: Viscous oil; $R_f$ (70% ethyl acetate in hexane): 0.20; $^1$H-NMR (300 MHz, CDCl$_3$) δ7.30–7.20 (m, 2H), 7.00–6.90 (t, 3H), 5.75 (d,1H), 4.15–4.00 (m, 1H), 3.80–3.60 (m, 6H), 3.40–3.30 (q, 1H), 3.20–3.10 (m, 4H), 2.90 (q, 1H), 2.70 (m, 1H), 2.35 (dd, 1H), 1.60–1.10(m, 6H), 1.00–0.80 (m, 12H).

Example 20
Synthesis of Aldehydes 16f–g

These compounds were synthesized following the same procedure as described for the syntheses of the compounds 16a–d. Yield was 50–60%.

16f: Isomer I: White solid, mp 45°–65° C. (softening to melt); $R_f$(70% ethyl acetate in hexane): 0.58; $^1$H-NMR (300 MHz, CDCl$_3$) δ9.60 (s, 1H), 8 7.30–7.10 (m, 9H), 6.75 (d, 1H), 4.70–4.50 (m, 3H), 3.90–3.50 (m, 2H), 3.20–2.60 (m, 6H), 2.40–2.30 (m, 1H), 1.80–1.20 (m, 3H), 1.00–0.80 (m, 6H).

16f: Isomer II: White gum, $R_f$ (70% ethyl acetate in hexane): 0.41; $^1$H-NMR (300 MHz, CDCl$_3$) δ9.50 (d, 1H), 7.40–7.10 (m, 9H), 6.60 (t, 1H), 4.70–4.50 (m, 3H), 3.90–3.50 (m, 2H), 3.20–2.60 (m, 6H), 2.40–2.30 (m, 1H), 1.70–1.10 (m, 3H), 1.00–0.80 (m, 6H).

16g: Isomer I: White gum, $R_f$ (70% ethyl acetate in hexane): 0.57; $^1$H-NMR (300 MHz, CDCl$_3$) δ9.55 (s, 1H), 7.30 (d, 2H), 6.90 (m, 3H), 6.45 (d, 1H), 4.40 (m, 1H), 3.80–3.60 (m, 4H), 3.15 (m, 4H), 3.00 (m, 1H), 2.80 (q, 1H), 2.40–2.30 (dd, 1H), 1.80–1.60 (m, 4H), 1.45 (m, 1H), 1.20 (m, 1H), 1.00–0.80 (m, 12H).

16g: Isomer II: White gum, $R_f$ (70% ethyl acetate in hexane): 0.42; $^1$H-NMR (300 MHz, CDCl$_3$) δ9.40 (s, 1H), 7.20 (m, 2H), 6.80 (m, 3H), 6.45 (d, 1H), 4.35 (m, 1H), 3.80–3.50 (m, 4H), 3.15 (m, 4H), 3.00 (m, 1H), 2.80 (q, 1H), 2.40–2.30 (dd, 1H), 1.80–1.60 (m, 4H), 1.45 (m, 1H), 1.20 (m, 1H), 1.00–0.80 (m, 12H).

The synthesis of compounds of Formula 26–32 are summarized in Scheme V below:

SCHEME V

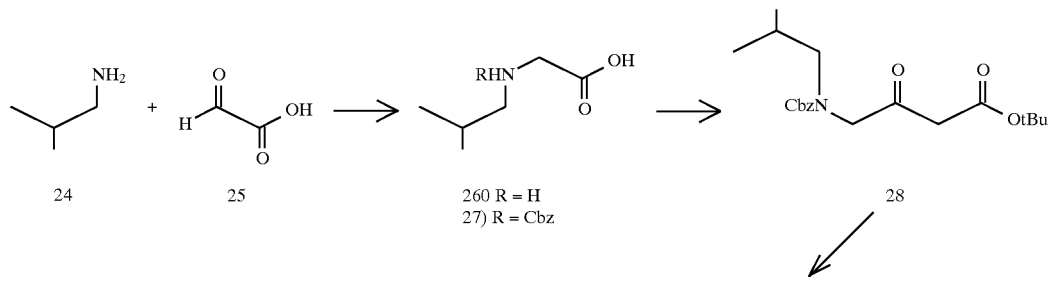

24   25   26) R = H   28
         27) R = Cbz

-continued
SCHEME V

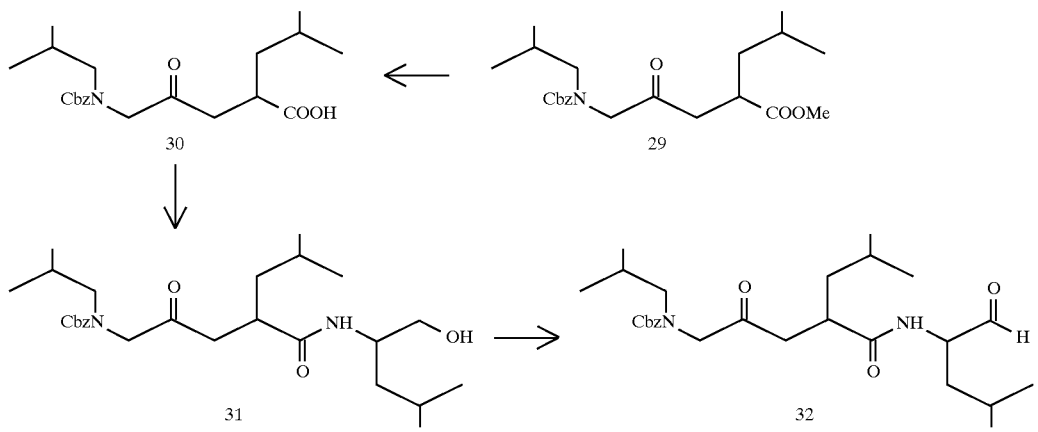

Example 21
Synthesis of Intermediates 26–27

A mixture of isobutyl amine (24, 7.36 g), glyoxylic acid (25, 5 g), water (30 mL) and 10% Pd-C(1 g) was hydrogenated (40 psi) in a Parr apparatus for 4 hours. Filtration and concentration of the reaction mixture at high vacuum gave compound 26 in quantitative yield. A sample of this material (2.48 g) was dissolved in acetonitrile-water (1:1, 40 mL), the solution was cooled to 0° C., and to it was added 5.20 g of N-(benzyloxycarbonyloxy)succinimide in portions. The icebath was removed and the reaction mixture was stirred for an additional hour. Acetonitrile was removed in the rotavapor, base was added to pH 9–10 and the layer was washed several times with a mixture of ether and hexane (1:1). The aqueous layer was then acidified (solid citric acid) to pH 3–4 and extracted into ethyl acetate (3×40 mL). Drying ($MgSO_4$) and solvent evaporation gave compound 27 which was used without further purification.

27: White gum; $^1$H-NMR (300 MHz, $CDCl_3$) shows 2 rotamers; δ7.40–7.20 (m, 5H), 5.20 and 5.15 (2 singlets, 2H), 4.10 and 4.00 (2 singlets, 2H), 3.15 (2 overlapping doublets, 2H), 2.90 (m, 1H), 0.90 (m, 6H).

Synthesis of Intermediate 28

This material was synthesized following the same general procedure as described above for the synthesis of compounds 2a–e. Thus, 5.06 g of compound 27 was converted to 3.32 g of compound 28.

28: Colorless oil; $R_f$ (20% ethyl acetate in hexane); 0.50; $^1$H-NMR (300 MHz, $CDCl_3$) shows 2 rotamers; δ 7.40–7.20 (m, 5H), 5.15 and 5.10 (2 singlets, 2H), 4.20 and 4.15 (2 singlets, 2H), 3.40 and 3.30 (2 singlets, 2H), 3.15 (2 overlapping doublets, 2H), 1.90 (m, 1H), 1.50 and 1.40 (2 singlets, 9H), 0.90 (m, 6H).

Synthesis of Intermediate 29

This material was synthesized following the same general procedure as described above for the synthesis of compounds 4a–e. Thus, 3.30 g of compound 28 was converted to 1.41 g of compound 29.

29: Viscous oil; $R_f$ (20% ethyl acetate in hexane); 0.50; $^1$H-NMR (300 MHz, $CDCl_3$) shows 2 rotamers; δ7.40–7.20 (m, 5H), 5.20–5.10 (2 sets of dd, 2H), 4.20–3.90 (m, 3H), 3.70 and 3.60 (2 singlets, 3H), 3.20–1.10 (a series of multiplets, 8H), 0.90 (m, 12H).

Synthesis of Intermediate 30

This material was synthesized following the same general procedure as described above for the synthesis of compounds 5a–e. Thus, 0.52 g of compound 29 was converted to 0.50 g of compound 30. $^1$H-NMR (300 MHz, $CDCl_3$) shows absence of rotameric methyl peaks at δ3.70 and 3.60.

Synthesis of Intermediate 31

This material was synthesized following the same general procedure as described above for the synthesis of compounds 15 a–d. Thus, 0.49 g of compound 30 was converted to 0.44 g of compound 31.

31: White gum; $R_f$ (5% methanol in methylene chloride); 0.52; $^1$H-NMR (300 MHz, $CDCl_3$) δ7.40–7.20 (m, 5H), 5.90 and 5.70 (2 sets of d, 1H), 5.20–5.00 (2 sets of dd, 2H), 4.20–3.40 (3 sets of m, 3H), 3.20–1.10 (a series of multiplets, 15H), 0.90 (m, 18H).

Synthesis of Aldehyde 32

This material was synthesized following the same general procedure as described above for the synthesis of compounds 16a–d. Thus, 0.43 g of compound 31 was converted to 0.20 g of compound 32.

32: White solid, mp 93°–95° C.; $R_f$ (5% methanol in methylene chloride): 0.53; $^1$H-NMR (300 MHz, $CDCl_3$) δ9.55 (s, 1H), 7.40–7.20 (m, 5H), 6.15 and 6.00 (2 sets of d, 1H), 5.20–5.00 (2 sets of dd, 2H), 4.50–3.70 (3 sets of m, 3H), 3.20–1.10 (a series of multiplets, 12H), 0.90 (m, 18H).

Example 22A
Inhibition and Rate of Inactivation of Cysteine Protease Activity To evaluate inhibitory activity, stock solutions (40 times concentrated) of each compound to be tested were prepared in 100% anhydrous DMSO and 5 μL of each inhibitor preparation were aliquoted into each of three wells of a 96-well plate. Calpain I, prepared by a modification of the method of W. J. Lee et al. (*Biochem. Internatl.* 22: 163–171 (1990)), was diluted into assay buffer (i.e., 50 mM Tris, 50 mM NaCl, 1 mM EDTA, 1 mM EGTA, and 5 mM-mercaptoethanol, pH 7.5 including 0.2 mM Succ-Leu-Tyr-MNA) and 175 μL aliquoted into the same wells containing the independent inhibitor stocks as well as to positive control wells containing 5 μL DMSO, but no compound. To start the reaction, 20 μL of 50 mM $CaCl_2$ in assay buffer was added to all wells of the plate, excepting three, which were used as background signal baseline controls. Substrate hydrolysis was monitored every 5 minutes for a total of 30 minutes using a Fluoroskan II fluorescence plate reader. Substrate hydrolysis in the absence of inhibitor was linear for up to 15 minutes.

Inhibition of calpain I activity was calculated as the percent decrease in the rate of substrate (S) hydrolysis in the presence of inhibitor ($_i$) relative to the rate in its absence ($_o$) Comparison between the inhibited and control rates was made within the linear range for substrate hydrolysis. For screening, compounds were tested at 10 μM. Compounds having 50% inhibition at 10 μM were considered active. The IC50s of inhibitors (concentration yielding 50% inhibition) were determined from the percent decrease in the rates of substrate hydrolysis in the presence of five to seven different concentrations of the test compound. The results were plotted as % inhibition versus log inhibitor concentration and the IC50 was calculated from linear regression of the data. Apparent second order rate constants were determined from analysis of reaction progress curves under pseudo-first order conditions. Each determination represents the means of three or more independent single cuvette analyses continually monitored via a Perkin-Elmer LS50B spectrofluorimeter. The rate of inhibition of hydrolysis was obtained by fitting the curve to the exponential equation (1):

$$y = Ae^{-(K_{obs} \cdot t)} + B \quad (1)$$

where y is the product formed at time t. $K_{obs}$ is the pseudo-first order rate constant for inactivation. A and B are constants. A, the amplitude of the reaction, is given by $[P_o - P_\infty]$ and B ($= P_\infty$) is the maximal product formed when the reaction is complete. The apparent second order rate constant $k_{app}$ was determined as $K_{obs}/[I]$. This was corrected for the presence of substrate to give the second order rate constant $k_2$ according to equation (2):

$$k_2 = k_{app} (1 + [S]/K_m) \quad (2)$$

addition of 100 ul of 2× concentrated stock dilution of substrate in assay buffer. Substrate hydrolysis was monitored using a Fluoroskan II (ex=390 nm; em=460 nm). Results are presented in Table II.

Example 22B

Inhibition of Serine Protease Activity

To demonstrate activity against the serine protease α-chymotrypsin (Sigma Chem. Co. Cat. #C-3142) the protocol of Example 22A was followed except that the enzyme was diluted into assay buffer consisting of 50 mM Hepes (pH 7.5)/0.5M NaCl and the final substrate concentration used was 0.03 mM Succ-Ala-Ala-Pro-Phe-AMC (Bachem, Inc. Cat. #I-1465). Additionally, because a-chymotrypsin is not a calcium sensitive enzyme and is constitutively active, following addition of inhibitor stocks to the 96 well plates, 100 μl of a 2-fold concentrated stock of enzyme in dilution buffer was first added and the reaction started by addition of 100 μl of a 2-fold concentrated stock of substrate in assay buffer. Substrate hydrolysis was monitored every 5 minutes up to 30 minutes using a Fluoroskan II (em=390 nm ex=460 nm). Results, expressed as inhibition of α-chymotrypsin at 10 μM, are presented in Table II.

Inhibition of thrombin (Sigma Chem. Co. Cat. #T-7009) was evaluated as described for chymotrypsin except that the assay was performed in 50 mM Tris, 10 mM $CaCl_2$, pH 7.5 and the substrate was 25 μM Bz-Phe-Val-Arg-AMC (Bachem cat#I-1080). Results are presented in Table II.

TABLE II

| Compnd. | Chemical Name | Calpain IC50 (nM) | Calpain Inactivation Rates (M-1s-1) | Cat B % I @ 1 μM | Cat L % I @ 1 μM | Thrombin % I @ 10 μM | Chymotrypsin % I @ |
|---|---|---|---|---|---|---|---|
| 32 | Z-N(iBu)CH$_2$COCH$_2$CH(iBu)CONH-Leu-H | 71 | | | | | |
| 16a | Ph(CH$_2$)$_4$COCH$_2$CH(iBu)CO-Leu-H | 138 | | 97 | 100 | 0 | 61 |
| 16c | Ph$_2$CHCOCH$_2$CH(iBu)CO-Leu-H | 50 | | 97 | 100 | 1 | 62 |
| 16d | Xanthene-COCH$_2$CH(iBu)CO-Leu-H | 25 | | 76 | 100 | 25 | 98 |
| 16b | CH$_3$CH$_2$CH(Ph)COCH$_2$CH(iBu)CO-Leu-H | 55 | | 99 | 100 | 0 | 21 |
| 8f | Xanthene-CO(CH$_2$CH(iBu)CO-Leu-CONHEt | 130 | | 98 | 100 | 13 | 93 |
| 14b | Xanthene-COCH$_2$CH(iBu)CO-Phe-CH$_2$F | | 75600 | | | 9 | 98 |
| 8d | Xanthene-COCH$_2$CH(iBu)CO-Abu-CONHEt | 485 | | 78 | 100 | 10 | 7 |
| 14a | CH$_3$CH$_2$CH(Ph)COCH$_2$CH(iBu)CO-Phe-CH$_2$F | | 5800 | | | 0 | 33 |
| 8c | Ph$_2$CHCOCH$_2$CH(iBu)CO-Abu-CONHEt | 1725 | | 100 | 100 | 0 | 6 |
| 8b | CH$_3$CH$_2$CH(Ph)COCH$_2$CH(iBu)CO-Abu-CONHEt | 6685 | | 84 | 98 | 0 | 0 |
| 14c | Z-Leu-CH$_2$CH(iBu)CO-Phe-CH$_2$F | | 16800 | | | 0 | 82 |
| 8a | Ph(CH$_2$)4COCH$_2$CH(iBu)CO-Abu-CONHEt | 8440 | | 10 | 81 | 0 | 0 |
| 8e | Z-Leu-CH$_2$CH(iBu)CO-Abu-CONHEt | 380 | | 100 | 95 | 0 | 0 |
| 16g-I | Ph-Piperazine-COCH$_2$CH(iBu)CO-Leu-H | 227 | | 100 | 97 | 0 | 0 |
| 16g-II | Ph-Piperazine-COCH$_2$CH(iBu)CO-Leu-H | 4500 | | 67 | 35 | 0 | 0 |
| 16f-I | 2-THIQ-COCH$_2$CH(iBu)CO-Phe-H | 28 | | 100 | 96 | 0 | 39 |
| 16f-II | 2-THIQ-COCH$_2$CH(iBu)CO-Phe-H (Diastereomer) | 1000 | | 71 | 52 | 0 | 12 |

To demonstrate activity against two other cysteine proteases, cathepsin B (Calbiochem, cat#219364) and cathepsin L (Calbiochem, cat#219402), assays were performed substantially the same as outlined above except that the cathepsin B and cathepsin L were diluted into a different assay buffer consisting of 50 mM sodium acetate (pH 6.0)/1 mM EDTA/1 mM dithiothreitol and the substrate used was Cbz-Phe-Arg-AMC (Bachem cat# I-1160; 0.1 mM for cathepsin B; 0.006 mM for cathepsin L). Additionally, the order of reagents added to the plate was altered because both enzymes are constitutively active. Following inhibitor addition to the plates, appropriate 2× concentrated stock dilutions of the enzyme preparations were made in assay buffer and 100 ul added to each well. The assay was initiated by It is intended that each of the patents, publications, and other published documents mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:
1. A compound of the formula:

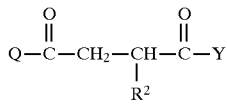

wherein:
Q is xanthene-9-yl;
Y has the formula:

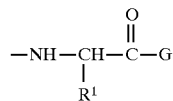

wherein:
$R^1$ and $R^2$ are independently H, alkyl having from one to about 14 carbons, cycloalkyl having from 3 to about 10 carbons, or a natural or unnatural side chain of an L-amino acid, said alkyl and cycloalkyl groups being optionally substituted with one or more J groups;
J is halogen, lower alkyl, aryl, amino optionally substituted with one to three aryl or lower alkyl groups, guanidino, alkoxycarbonyl, aralkoxycarbonyl, alkoxy, hydroxy, or carboxy; and
G is hydrogen; $C(=O)NR^3R^4$; $CH_2R^5$ or $C(=O)OR^3$;

wherein:
$R^3$ and $R^4$ are each independently hydrogen, alkyl having from 1 to about 10 carbons, said alkyl groups being optionally substituted with one or more J groups, aryl having from about 6 to about 14 carbons, and aralkyl having from about 7 to about 15 carbons; and
$R^5$ is halogen;
with the proviso that if G is hydrogen and Q is alkyl substituted with J, and said J is an α-amino group, then the α-amino nitrogen must be tertiary.

2. The compound of claim 1 wherein $R^2$ is isobutyl.
3. The compound of claim 1 wherein $R^1$ is isobutyl, benzyl or ethyl.
4. The compound of claim 1 wherein G is hydrogen, —C(=O)NHC$_2$H$_5$, or —CH$_2$F.
5. The compound of claim 1 wherein $R^2$ is isobutyl, $R^1$ is isobutyl, benzyl or ethyl, and G is hydrogen, —C(=O)NHC$_2$H$_5$, or —CH$_2$F.
6. The compound of claim 5 wherein Q is xanthen-9-yl.
7. A composition for inhibiting a serine protease or a cysteine protease comprising a compound of claim 1.
8. A method for inhibiting serine proteases or cysteine proteases comprising contacting a protease selected from the group consisting of serine proteases and cysteine proteases with an inhibitory amount of a compound of claim 1.

* * * * *

UNITED STATES PATENT AND TRADEMARK OFFICE
CERTIFICATE OF CORRECTION

PATENT NO. : 5,827,877  
DATED : October 27, 1988  
INVENTOR(S) : Chatterjee

Page 1 of 3

It is certified that error appears in the above-indentified patent and that said Letters Patent is hereby corrected as shown below:

On the cover page, first column, under "OTHER PUBLICATIONS", at "Greene and Wuts", second line thereof, please delete "Wiley & sons, 1991." and insert --Wiley & Sons, 1991.-- therefor.

On the cover page, second column, under "OTHER PUBLICATIONS", at "Hamada", second line thereof, please delete "and $^{t1}$" and insert --and $B_1^t$-- therefor.

On the cover page, second column, under "OTHER PUBLICATIONS", at "Hoffman", second line thereof, please delete "2-Alky-4Ketoacids" and insert --2-Alkyl-4Ketoacids-- therefor.

On the cover page, second column, under "OTHER PUBLICATIONS", at "Hoffman, R.V. and Kim", second line thereof, please delete "using" and insert --Using-- therefor.

On the cover page, second column, under "OTHER PUBLICATIONS", at "Luly", second line thereof, please delete "$\gamma$-Amino Acids" and insert --$\alpha$-Amino Acids-- therefor.

In column 2, line 64, please delete "about carbons" and insert --about 10 carbons-- therefor.

In column 12, line 38, please delete "(m, 12H);" and insert --(m, 12H).-- therefor.

In column 12, line 55, please delete "(m, 9H);" and insert --(m, 9H).-- therefor.

UNITED STATES PATENT AND TRADEMARK OFFICE
CERTIFICATE OF CORRECTION

PATENT NO. : 5,827,877
DATED : October 27, 1998
INVENTOR(S) : Chatterjee

It is certified that error appears in the above-indentified patent and that said Letters Patent is hereby corrected as shown below:

In column 12, line 64, please delete "Diastereomeric" and insert --Diastereomers-- therefor.

In column 13, line 6, please delete "Diastereomeric" and insert --Diastereomers-- therefor.

In column 13, line 13, please delete "Diastereomeric" and insert --Diastereomers-- therefor.

In column 17, Scheme III, please delete

"

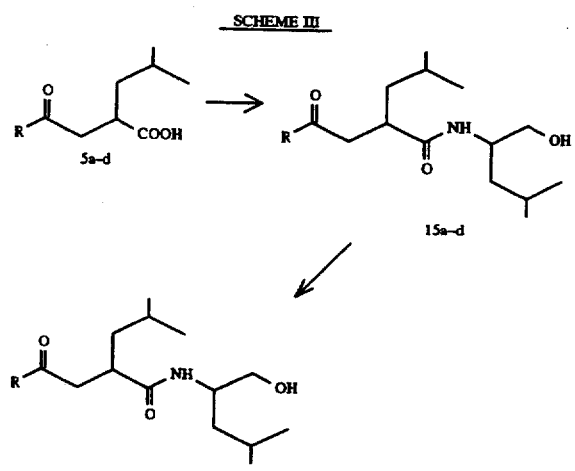

UNITED STATES PATENT AND TRADEMARK OFFICE
CERTIFICATE OF CORRECTION

| | |
|---|---|
| PATENT NO. : | 5,827,877 |
| DATED : | October 27, 1998 |
| INVENTOR(S) : | Chatterjee |

It is certified that error appears in the above-indentified patent and that said Letters Patent is hereby corrected as shown below:

and insert

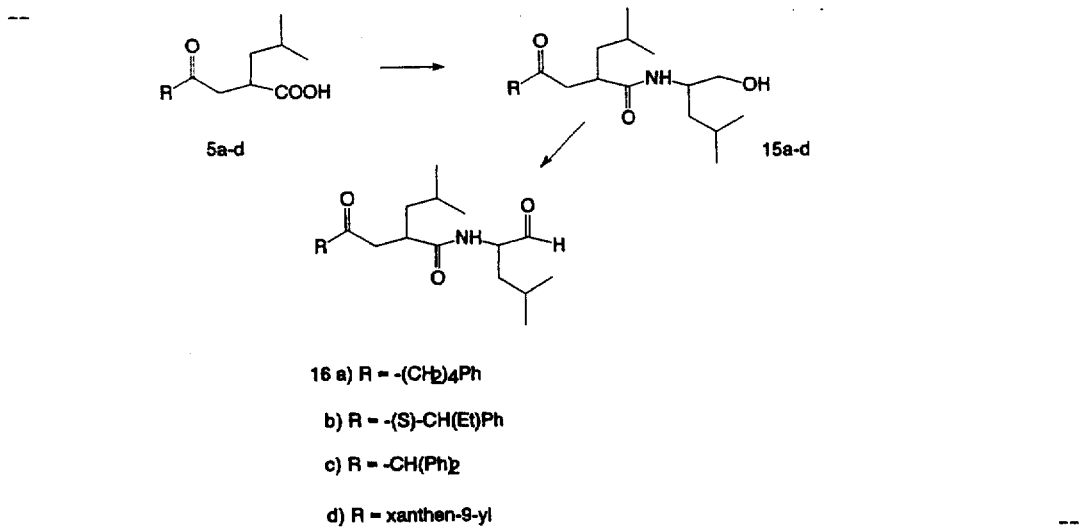

In column 18, line 32, please delete "10" at the end of the line.

In column 23, line 49, please delete "6 7.40-7.20" and insert --δ 7.40-7.20-- therefor.

In column 26, line 15, please delete "a-chymotrypsin" and insert --α-chymotrypsin-- therefor.

Signed and Sealed this

Fourth Day of January, 2000

Attest:

Attesting Officer

*Acting Commissioner of Patents and Trademarks*